United States Patent [19]

Haseltine, Jr.

[11] 4,064,068
[45] Dec. 20, 1977

[54] PREPARATION OF ISOPROPYLNAPHTHALENE MIXTURE

[75] Inventor: Marcus W. Haseltine, Jr., Brookhaven, Pa.

[73] Assignee: Sun Oil Company of Pennsylvania, Philadelphia, Pa.

[21] Appl. No.: 600,672

[22] Filed: July 30, 1975

[51] Int. Cl.² .............................................. B01F 1/00
[52] U.S. Cl. ..................................... 252/364; 8/94 R
[58] Field of Search .............................. 252/364, 316; 260/668 B; 8/94

[56] References Cited

U.S. PATENT DOCUMENTS

| | | | |
|---|---|---|---|
| 2,800,457 | 7/1957 | Green et al. | 252/316 |
| 3,627,581 | 12/1971 | Phillips, Jr. | 252/316 X |
| 3,806,463 | 4/1974 | Konishi et al. | 252/316 |

FOREIGN PATENT DOCUMENTS 915,342  1/1963  United Kingdom ...................... 8/94

*Primary Examiner*—Benjamin R. Padgett
*Assistant Examiner*—Josephine Lloyd
*Attorney, Agent, or Firm*—J. Edward Hess; Donald R. Johnson; Paul Lipsitz

[57] ABSTRACT

A process for the preparation of a mixture of alkylnaphthalenes useful as a dye solvent for carbonless copy paper by:

1. alkylating naphthalene in the presence of an alkylation catalyst,
2. adding an additional amount of catalyst after the alkylation has been completed, and
3. holding the reaction mass at 180° to 280° F. for a time sufficient to maximize yield of dialkylated product.

13 Claims, No Drawings

PREPARATION OF ISOPROPYLNAPHTHALENE MIXTURE

Alkylated naphthalenes and their mixtures are known as useful dye solvents and, in particular, a mixture of mono-, di-, and tri-isopropyl naphthalenes is a known dye solvent for the preparation of microcapsules for pressure sensitive record material; e.g., carbonless copy systems (see for example U.S. Pat. No. 3,806,463). It is also known that a composition comprising from about 25% to about 35% by weight of monoisopropyl naphthalene, no less than about 55% up to about 60% of diisopropylnaphthalene, and about 10% triisopropyl naphthalene is a superior composition in that it has excellent dye solubility, low odor and other characteristics needed for commercial acceptance.

It is also known that naphthalene may be alkylated using an aluminum chloride or other alkylation catalysts to give a mixture of alkylnaphthalenes. However, when the alkylation is carried out in the usual manner, the proportion of dialkylnaphthalene in the product is not obtained in significantly high yield to permit economic commercial production of the above described dye solvent.

It has now been found that by employing the specific alkylation procedure of this invention the proportion of dialkylated product may be significantly increased and a high yield of the specific preferred dye solvent product can be obtained. In accord with the invention naphthalene is alkylated in the presence of an alkylation catalyst and when the alkylation is completed an additional amount of catalyst is added and the reaction mass held at a temperature of from about 180° to about 280° F. for a time sufficient to maximize yield of dialkylated product. In a further more specific embodiment the invention provides a process for the preparation of a mixture of isopropylnaphthalenes comprising about 25% to about 35% monoisopropyl naphthalene, no less than about 55% up to about 60% diisopropylnaphthalene and less than about 10% triisopropyl naphthalene which comprises the steps of:

1. adding propylene to naphthalene at a temperature of from about 180° to about 280° F. and in the presence of from about 0.5% to about 2% by weight of naphthalene of a strong acid alkylation catalyst $AlCl_3$ preferably the mole ratio of propylene to naphthalene being from about 1.3:1 to about 2.3:1,
2. adding an additional 0.2% to 1.0% of catalyst after said propylene has been added and
3. holding the reaction mass at 180° to 280° F. for about 15 to about 60 minutes.

It will be understood that the alkylation may be carried out with conventional alkylation agents, e.g., alkylhalides, preferably chlorides, but preferably olefins of from two to about 10 carbon atoms will be used; e.g. ethylene, propylene, the butenes, pentenes, hexenes, heptenes, octenes, nonenes, and decenes. Likewise, the alkylation catalysts will include those normally used in alkylations, but will preferably be Friedel-Crafts catalysts and most preferably a strong acid Friedel-Crafts catalyst such as metal halides; e.g., aluminum chloride, zinc chloride, and the like. It will also be understood that the catalysts may be employed as the conventional complexes; e.g., $AlCl_3$-hydrocarbon complexes.

Further illustrative discussion of the process of the invention will be made in terms of the alkylation of naphthalene with propylene using $AlCl_3$ as catalyst to give that specific dye solvent composition referred to above.

In carrying out the process of the invention the usual alkylation equipment may be used. The naphthalene is heated to about 180° F. and the first charge of catalyst is mixed in. Then the propylene is fed in, during which time the temperature is allowed to rise to about 250° F. The amount of catalyst used will be from about 0.5 to about 2%, preferably 1% by weight of the naphthalene, and the propylene will be from about 1.3 to 2.0 moles, preferably from about 1.4 to about 1.7 moles per mole of naphthalene. When the propylene is completely added, stirring at about 250° is continued and then an additional 0.5 to 1% of aluminum chloride catalyst is added. The reaction mass is held on temperature, preferably at about 250° F. for a period of time of from about 15 to about 60 minutes. This holding period is also essential to the process for without it no significant increase of dialkylnaphthalene is obtained and a much lower yield of product is obtained. During the holding period it is quite probable that transalkylation occurs, but it should be noted that this transalkylation occurs in the absence of any added naphthalene.

When the holding time is completed the reaction mass contains excess naphthalene, spent catalyst and the composition desired for use as a carbonless paper solvent. To work up the product, it is allowed to stand to allow the catalyst complex to settle and this is withdrawn from a bottom valve. The remaining organic layer is then neutralized with an aqueous caustic solution at elevated temperature (about 200° F.) to remove dissolved aluminum chloride. After mixing, settling and separating off the aqueous layer, the organic layer is washed once or twice with hot (200° F.) water.

The organic material is then subjected to distillation and the excess naphthalene (about 5% by weight) removed and a small amount of the mono-isopropylnaphthalene also distills off. The residual product contains the components of the desired solvent in essentially the desired proportions and in good yield, but there is also present colored heavy end products which may be separated by distilling off the product at a temperature up to about 650° F. While the product might be used directly at this point, it is frequently desirable, in order to obtain a product of higher purity and quality, to distill off each of the fractions separately and recombine them in the desired proportion to make the final product. In making up the final solvent from the separate components it is preferred to make the solvent composition contain about 30% monoisopropylnaphthalene, about 60% diisopropylnaphthalene and no more than about 10% triisopropylnaphthalene. It will also be understood that some small amount of by-product materials may be present, but these will not detract from the usefulness of the product.

The high yield of product obtained by the process of the invention is dependent upon both the step of adding additional $AlCl_3$ catalyst and also upon the step of holding the reaction mass on temperature to allow the transalkylation to occur whereby the amount of dialkyl product is increased. If either one of these steps is omitted yield of solvent product falls off dramatically. A significant advantage to the process of the invention lies in the fact that most of the alkylated product is useable for the solvent composition and this will be illustrated by the examples which follow which are directed to preparation of the solvent composition comprising about 25% to 35% moniisopropylnaphthalene, no less than about 55%, up to about 60% diisopropylnaptha-
lene, and less than about 10% triisopropylnaphthalene.

EXAMPLE 1

A propylation was carried out in which naphthalene was propylated using 1% AlCl₃, but no second addition of AlCl₃ or holding period occured.

Petroleum grade naphthalene (512g.) was added to a glass reactor and brought to a temperature of 180° F. Aluminum chloride (5.1 grams) was quickly added and a propylene bubbler was turned on. Temperature was allowed to rise to no higher than 250° F and the propylene addition rate was set such that the propylation was completed in one hour after 1.9 moles per mole of naphthalene had been added. When the propylene addition was completed a 10 cc sample of the reaction mixture was removed and immediately washed with 10 volume percent of a 20 weight percent caustic solution. The reaction product was then water washed until neutral. The sample was dried over Drierite and submitted for analysis by gas chromatography. The product represented a 53% yield of carbonless paper solvent (CPS) obtainable from the product.

EXAMPLE 2

In this experiment the naphthalene propylation was followed by addition of another 1% AlCl₃ plus a holding time. The procedure used was the same as that of Example 1 except that after the desired propylene had been added, an additional 5.1 grams of aluminum chloride were added to the reactor mixture. The reaction mixture was then held at 250° F. for 30 minutes. During this holding time the mixture was stirred vigorously. Work-up and analysis of the samples were the same as those described in Example 1. The product represented a 71% yield of solvent obtainable from the product.

EXAMPLE 3

When Examples 1 and 2 were repeated as described above, but at various ratios of propylene to naphthalene the yields of products shown in the following Table I were obtained.

TABLE I

| Molar Ratio of Propylene to Naphthalene | Percent Yield of Solvent | |
|---|---|---|
| | Control Process of Example 1 | Process of The Invention (Example 2) |
| 1.4:1 | 53 | 76 |
| 1.5:1 | 54 | 83 |
| 1.6:1 | 54 | 88 |
| 1.7:1 | 54 | 86 |
| 1.8:1 | 54 | 83 |
| 1.9:1 | 53 | 71 |
| 2.0:1 | 50 | — |

EXAMPLE 4

In this experiment the propylation was followed by a half hour holding period without additional AlCl₃ being added. Only a slight yield improvement was obtained. Then AlCl₃ was added and the reaction mass held on temperature in accord with the invention to give a significant yield improvement. The details follow:

The procedure used was the same as that of Example 1 except that after the desired propylene had been added, the reaction mixture as held at 250° F. for 30 minutes, under vigorous stirring. Samples were taken at this point to determine yield of solvent. Then 5.1 grams of aluminum chloride were added to the reactor and the reaction mixture was held at 250° F. for an additional 30 minutes. Samples were again taken for work-up and analysis as in Example 1.

Table II illustrates the data obtained.

TABLE II

| Procedure | Percent By Weight | | | | Percent Yield |
|---|---|---|---|---|---|
| | Naphthalene | Isopropylnaphthalene | | | By-Products | |
| | | Mono- | Di | Tri | | CPS |
| 1. Propylation Only | 15 | 25 | 33 | 22 | 5 | 54 |
| 2. Proplyation + Holding Period | 12 | 25 | 39 | 22 | 2 | 65 |
| 3. Propylation + AlCl₃ + Holding Period | 7 | 26 | 53 | 12 | 2 | 88 |

It is clear from the above table that the process of the invention significantly increases the amount of dialkyl isomer formed which in turn contributes to the high yield of product.

The invention claimed is:

1. In the process of alkylating naphthalene with an alkylating agent in the presence of an alkylation catalyst to obtain a mixture of alkylated naphthalenes, the improvement of increasing the yield of dialkylnaphthalene which comprises adding additional catalyst after the alkylation is completed and then holding the reaction mass at a temperature of from about 180° to about 280° F. for a time sufficient to maximize yield of dialkylated product.

2. The process of claim 1 where the alkylating agent is an olefin containing from 2 to 10 carbon atoms.

3. The process of claim 2 where the catalyst is a Friedel-Crafts catalyst.

4. The process of claim 3 where the catalyst is aluminum chloride.

5. The process of claim 4 where alkylating agent is propylene.

6. A process for the preparation of a mixture of alkylnaphthalenes useful as dye solvent for carbonless copy paper which comprises the steps of
   a. adding an olefin alkylating agent containing from 2 to 10 carbon atoms to naphthalene at a temperature of from about 180° to about 280° F. and in the presence of from about 0.5% to about 2% by weight of naphthalene of a Friedel-Crafts catalyst,
   b. adding an additional 0.2% to 1.0% of catalyst after the alkylating agent has been added, and
   c. holding the reaction mass at 180° to 280° F for about 15 to about 60 minutes to maximize yield of dialkynaphthalene.

7. The process of claim 6 where the alkylating agent is propylene and the catalyst is aluminum chloride.

8. The process of claim 7 where the mole ratio of propylene to naphthalene is from about 1.3 to about 2.3.

9. A process for the preparation of a mixture of isopropylnaphthalenes useful as a dye solvent for carbonless copy paper said mixture comprising by weight from about 25% to about 35% of monoisopropylnaphthalene, no less than about 55% up to about 60% of diisopropylnaphthalene, and about 10% of triisopropylnaphthalene which comprises the steps of
   a. adding propylene to naphthalene at a temperature of from about 180° to about 280° F. and in the presence of from about 0.5% to about 2% by weight of naphthalene of AlCl₃ as alkylation catalyst, the mole ratio of propylene to naphthalene being from about 1.3 to about 2.3, b. adding an additional 0.2% to 1.0% of AlCl₃ after the propylene has been added, and
c. holding the reaction mass at 180° to 280° F. for about 15 to about 60 minutes to maximize yield of solvent.

10. The process of claim 9 where the mole ratio of propylene to naphthalene is from about 1.4 to about 1.7.

11. The process of claim 9 where the isopropylnaphthalene mixture comprises about 30% monoisopropylnaphthalene, about 60% diisopropylnaphthalene and no more than about 10% triisopropylnaphthalene.

12. The process of claim 11 where the amount of AlCl₃ added in each of step 1 and step 2 is about 1%.

13. The process of claim 12 where the ratio of propylene to naphthalene is from about 1.4 to about 1.7.

* * * * *